United States Patent [19]

Fischer et al.

[11] Patent Number: 5,412,120
[45] Date of Patent: May 2, 1995

[54] PREPARATION OF CARBOXYLIC ESTERS

[75] Inventors: Rolf Fischer, Heidelberg; Norbert Goetz, Worms; Thomas Kuekenhoehner, Boehl-Iggelheim; Werner Schnurr, Herxheim, all of Germany

[73] Assignee: BASF Aktiengesellschaft, Ludwigshafen, Germany

[21] Appl. No.: 158,361

[22] Filed: Nov. 29, 1993

Related U.S. Application Data

[63] Continuation-in-part of Ser. No. 990,269, Dec. 14, 1992, abandoned.

[30] Foreign Application Priority Data

Dec. 13, 1991 [DE] Germany .................. 41 41 223.0

[51] Int. Cl.⁶ .......................................... C07D 315/00
[52] U.S. Cl. .................... 549/427; 560/129; 560/124; 560/1
[58] Field of Search ............... 560/129, 124, 1; 549/427

[56] References Cited

U.S. PATENT DOCUMENTS 5,252,755  10/1993  Henkelman et al. .......... 549/427

OTHER PUBLICATIONS

Chem. Abstr., vol. 109, 14924 (1970).
Tetrahedron Lett. 27 1986, 2283–2286.

*Primary Examiner*—Johann Richter
*Assistant Examiner*—John Peabody
*Attorney, Agent, or Firm*—Keil & Weinkauf

[57] ABSTRACT

A process for preparing monocarboxylic esters of the general formula I

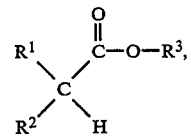

where
$R^1$ and $R^2$ are each hydrogen, $C_1$–$C_{12}$-alkyl, $C_3$–$C_8$-cyclo-alkyl acyl, aryl or $C_7$–$C_{20}$-aralkyl or together $-(CH_2)_n-X-(CH_2)_m-$,
X is methylene, oxygen, sulfur, NH or $NR^3$,
$R^3$ is $C_1$–$C_{12}$-alkyl, and
n and m are each from 0 to 8, comprises reacting geminal dicarboxylic esters of the general formula II

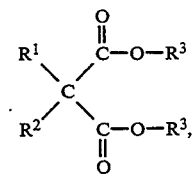

where $R^1$ to $R^3$ are each as defined above, at from 150° to 400° C. in the presence of catalysts.

6 Claims, No Drawings

PREPARATION OF CARBOXYLIC ESTERS

This application is a continuation-in-part of application Ser. No. 07/990,269, filed on Dec. 14, 1992, now abandoned.

The present invention relates to a process for preparing monocarboxylic esters by reacting geminal dicarboxylic esters at elevated temperatures in the presence of metal oxides.

It is known to convert geminal dicarboxylic esters into monocarboxylic esters in a three-stage reaction by alkaline hydrolysis to the corresponding geminal dicarboxylic acid, thermal elimination of one carboxyl group and esterification of the remaining carboxyl group (JP-A-62/201 843; Chem. Abstr.: Vol. 109, 14925). It is also known that by heating geminal dicarboxylic esters with mixtures of mineral and carboxylic acids it is possible to obtain the corresponding monocarboxylic acids (Arch. Pharm. 319, (1986), 29–37), which must then be esterified to obtain the desired monocarboxylic esters. It is additionally known, from Tetrahedron Lett. 27 (1986), 2283–2286, to convert geminal dicarboxylic esters into monocarboxylic esters in a single-stage reaction by heating in polar solvents such as dimethyl sulfoxide or dimethylformamide in the presence of alkali metal chlorides or cyanides.

The first two methods for preparing monocarboxylic esters from geminal dicarboxylic esters have the disadvantage of multiple reaction stages and, additionally in the first case, of producing salt. The third, single-stage synthesis requires very long reaction times.

It is an object of the present invention to remedy the aforementioned disadvantages.

We have found that this object is achieved by a novel and improved process for preparing monocarboxylic esters of the general formula I

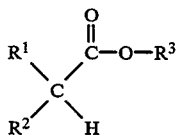

where
$R^1$ and $R^2$ are each hydrogen, $C_1$–$C_{12}$-alkyl, $C_3$–$C_8$-cycloalkyl, acyl, aryl or $C_7$–$C_{20}$-aralkyl or together $-(CH_2)_n-X-(CH_2)_m-$,
X is methylene, oxygen, sulfur, NH or $NR^3$,
$R^3$ is $C_1$–$C_{12}$-alkyl, and
n and m are each from 0 to 8,
which comprises reacting geminal dicarboxylic esters of the general formula II

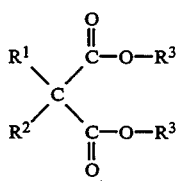

where $R^1$ to $R^3$ are each as defined above, at from 150° to 400° C. in the presence of catalysts to be defined.

The process of the invention can be carried out as follows:

The geminal dicarboxylic esters II are converted into the monoesters I by reaction over the catalysts at elevated temperatures.

The reaction can be carried out batchwise or continuously at from 150° to 400° C., preferably at from 200° to 400° C., in particular at from 250° to 350° C. The reaction pressure is not critical, but it is advantageous to employ pressures of from 1 to 100 bar, in particular of from 1 to 10 bar. The reaction of the geminal dicarboxylic diesters II to form monocarboxylic esters I can be carried out in the liquid phase or, preferably, in the gas phase. In either case it is advantageous to run the reaction with a weight hourly space velocity over the catalyst of from 0.1 to 10 g, in particular of from 0.1 to 5 g, of dicarboxylic ester II per g of catalyst per hour.

The reaction of the invention can be carried out in the absence of solvents. However, it can be advantageous to carry it out in the presence of solvents. Examples of suitable solvents are ethers such as diethyl ether, tetrahydrofuran and dioxane, aromatics such as benzene, toluene and xylenes, chlorinated hydrocarbons such as chloroform and methylene chloride, and alcohols of from 1 to 8, preferably of from 1 to 5, carbon atoms such as methanol, ethanol, n-propanol, isopropanol, butanols and pentanols. Alcohols have been found to be particularly advantageous. The amount of solvent relative to the geminal dicarboxylic diester II is from 5 to 90% by weight.

The reaction can be carried out batchwise or continuously as a fixed bed reaction using fixed bed catalysts, for example in the liquid phase by the upward or downward (trickle bed) flow procedure or in the gas phase, for example in a fluidized bed, or alternatively with fixed bed catalysts suspended in the liquid phase.

In the liquid phase the reaction of the geminal dicarboxylic ester II is carried out for example by heating a mixture of II with or without a solvent to the desired reaction temperature in the presence of a suspended fixed bed catalyst. After the reaction has ended, the reaction mixture is cooled down and the catalyst is removed, for example by filtration or neutralization. The reaction mixture can then be subjected to a fractional distillation to isolate the desired monocarboxylic ester I.

In a preferred embodiment of the process of the invention, the reaction is carried out in the gas phase over a fluidized bed catalyst and in the presence of an alcohol for example as follows: A mixture of II and the alcohol in question is gasified and then passed at the desired reaction temperature with or without an inert gas such as nitrogen, carbon dioxide or argon over the fluidized bed of catalyst. The reactor exit mixture is condensed by a suitable cooling means and then worked up by fractional distillation. The desired monocarboxylic ester I is separated off. Unconverted dicarboxylic ester II can be recycled into the reaction, if desired.

A very wide range of catalysts can be used, including mineral acids, sulfonic acids, carboxylic acids and Lewis acids. Examples of preferred metal oxides which are particularly suitable catalysts are boron trioxide, aluminum oxide, silicon dioxide, titanium dioxide, zinc oxide, niobium oxide, vanadium pentoxide, molybdenum oxide, cerium oxide and tungsten oxide, preferably aluminum oxide, silicon dioxide, titanium dioxide, zirconium dioxide, boron trioxide, vanadium pentoxide, oxides of chromium molybdenum oxide, tungsten oxide or mixtures thereof.

As acidic catalysts it is also possible to use acidic phosphates, acidic ion exchangers, silicates and zeolites, for example zeolites of the mordenite group, X-, Y- or L-zeolites, such as mordenite, erionite and faujasite, preferably zeolites having a pentasil structure such as ZSM-5, ZSM-11 and ZBM-10 zeolites, particularly preferably ZSM-5 and ZSM-11 zeolites.

Suitable acidic catalysts also include heteropoly acids such as $H_3[PW_{12}O_{40}]$, $H_3[PMo_{12}O_{40}]$ or $H_4[SiW_{12}O_{40}]$, preferably $H_3[DW_{12}O_{10}]$ and $H_3[PMo_{12}O_{40}]$, particulary preferably $H_3[PW_{12}O_{40}]$.

In the compounds I and II the link X, the substituents $R^1$, $R^2$ and $R^3$ and the indices n and m have the following meanings:

R$^1$ and $R^2$ are each independently of one another
  hydrogen,
  $C_1-C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl or isododecyl, preferably $C_1-C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethyl-propyl, n-hexyl, isohexyl, sec-hexyl, n-heptyl, isoheptyl, n-octyl, isooctyl, particularly preferably $C_1-C_4$-alkyl such as methyl, ethyl, n-propyl, isopropyl, n-butyl, isobutyl, sec-butyl or tert-butyl,
  $C_3-C_8$-cycloalkyl such as cyclopropyl, cyclobutyl, cyclopentyl, cyclohexyl, cycloheptyl or cyclooctyl, preferably cyclopentyl, cyclohexyl or cyclooctyl,
  acyl such as acetyl,
  aryl such as phenyl, 1-naphthyl, 2-naphthyl, 1-anthryl, 2-anthryl or 9-anthryl, preferably phenyl, 1-naphthyl or 2-naphthyl, particularly preferably phenyl,
  $C_7-C_{20}$-aralkyl, preferably $C_7-C_{12}$-phenylalkyl such as benzyl, 1-phenethyl, 2-phenethyl, 1-phenyl-propyl, 2-phenylpropyl, 3-phenylpropyl, 1-phenylbutyl, 2-phenylbutyl, 3-phenylbutyl or 4-phenylbutyl, particularly preferably benzyl, 1-phenethyl or 2-phenethyl,
  —$(CH_2)_n$—X—$(CH_2)_m$—,
X is methylene (—$CH_2$—),
  oxygen
  sulfur,
  NH,
  $NR^3$,
$R^3$ is $C_1-C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl or isododecyl, preferably $C_1-C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethyl-propyl, n-hexyl, isohexyl, sec-hexyl, n-heptyl, isoheptyl, n-octyl, isooctyl, particularly preferably $C_1-C_4$-alkyl such as methyl, ethyl, n-propyl, isopropyl, n-butyl, isobutyl, sec-butyl or tert-butyl, n and m are each an integer from 0 to 8, such as 0, 1, 2, 3, 4, 5, 6, 7 or 8, preferably an integer from 1 to 4, such as 1, 2, 3 or 4.

Suitable geminal dicarboxylic esters of the formula II are for example 2-substituted malonic diesters such as dimethyl 2-methylmalonate, diethyl 2-ethylmalonate, dimethyl 2-acetylmalonate, diethyl 2-phenylmalonate, dimethyl 2,2-dimethylmalonate, dipropyl 2,2-diacetylmalonate, dimethyl 2-benzylmalonate, dimethyl 1,1-cyclopropanedicarboxylate, diethyl 1,1-cyclohexanedicarboxylate, dimethyl tetrahydropyran-4,4-dicarboxylate, dimethyl tetrahydrothiopyran-4,4-dicarboxylate and dimethyl 1,1-cyclopentanedicarboxylate.

The dicarboxylic esters II required for the reaction of the invention are obtainable for example by mono- or bisalkylation or acylation of malonic diesters.

The monocarboxylic esters obtainable by the process of the invention are useful, versatile intermediates for organic synthesis.

EXAMPLES

EXAMPLES 1 TO 6

Dimethyl tetrahydropyran-4,4-dicarboxylate was converted into methyl tetrahydropyran-4-carboxylate by reaction in the gas phase over oxidic fixed bed catalysts with or without a solvent.

Example 1 was carried out without a solvent. The diester was pumped at various temperatures at a rate of 8 g per hour onto 5 g of $Al_2O_3$ situated in a helical stainless steel reactor. The reactor was heated to the desired temperature in a hot air oven. The gaseous exit mixture was condensed and analyzed by gas chromatography. The Table shows the composition of the reactor exit mixture at the indicated reaction time.

In Examples 2 to 6 solutions of the diester were pumped in at a rate of about 5 g of diester and about 5 g of solvent per hour. The liquid exit mixture (51.6 g) obtained in Example 3 at 270° C. after 6 hours was subjected to fractional distillation, yielding 18.7 g of methyl tetrahydropyran-4-carboxylate (82%, based on 32.2 g of diester used).

TABLE

Tetrahydropyran carboxylic ester (2) by gas phase cleavage of tetrahydropyran dicarboxylic ester (1)

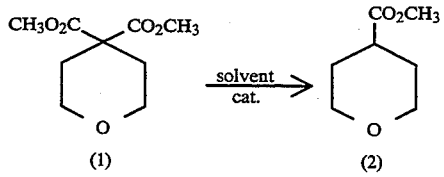

| Ex. | Catalyst (fixed bed) | Solvent Type | % wt. | Temp. [°C.] | Reaction time [h] | GC analyses (area %) (1) | (2) | Total by-product |
|---|---|---|---|---|---|---|---|---|
| 1 | Al₂O₃ | — | — | 270 | 3 | 81 | 11 | 8 |
|   |      |   |   | 300 | 2 | 88 | 7  | 5 |
|   |      |   |   | 350 | 2 | 61 | 22 | 17 |
| 2 |      | THF | 50 | 270 | 2 | 76 | 13 | 11 |
|   |      |     |    | 300 | 2 | 85 | 9  | 6 |
|   |      |     |    | 330 | 1 | 73 | 17 | 10 |
| 3 |      | CH₃OH | 50 | 270 | 4 | 6  | 86 | 8 |
|   |      |       |    | 300 | 2 | 5  | 45 | 50 |
| 4 | SiO₂ | CH₃OH | 50 | 270 | 2 | 94 | 4  | 2 |
|   |      |       |    | 300 | 2 | 88 | 11 | 1 |
|   |      |       |    | 350 | 1.5 | 74 | 25 | 1 |
|   |      |       |    | 400 | 1 | 50 | 48 | 2 |
|   |      |       |    | 450 | 1 | 34 | 60 | 6 |
| 5 | TiO₂ | CH₃OH | 50 | 270 | 2 | 67 | 31 | 2 |
|   |      |       |    | 300 | 2 | 46 | 53 | 1 |
|   |      |       |    | 350 | 2 | 20 | 76 | 4 |
|   |      |       |    | 400 | 1.5 | 18 | 62 | 20 |
| 6 | ZnO  | CH₃OH | 50 | 270 | 1.5 | 93 | 6 | 1 |
|   |      |       |    | 300 | 2 | 90 | 9 | 1 |
|   |      |       |    | 350 | 2 | 82 | 16 | 2 |
|   |      |       |    | 400 | 1.5 | 69 | 15 | 16 |

EXAMPLE 7

Per hour a solution of 4.4 g of dimethyl 2,2-dimethylmalonate in 4.4 g of methanol was passed over 5 g of aluminum oxide at 275° C. The exit mixture obtained over 6 hours (42.5 g) was distilled, yielding a mixture of 10.7 g of methyl isotyrate (64%, based on diester used) and 8 g of methanol.

EXAMPLE 8

Per hour a solution of 4.5 g of dimethyl 1,1-cyclohexanedicarboxylate in 4.5 g of methanol was passed at 275° C. over 5 g of aluminum oxide. The exit mixture obtained over 6 hours (36.5 g) was distilled to yield 10.1 g of methyl cyclohexanecarboxylate ( 53%, based on diester used) and 7.7 g of the starting material.

EXAMPLE 9

A solution of 4.5 g of diethyl 1,1-cyclopropanedicarboxylate in 4.5 g of ethanol was passed at 300° C. over 5 g of aluminum oxide. The reactor exit mixture was found to contain ( according to GC analysis) (area %) 58% of starting material, 35% of ethyl cyclopropanecarboxylate and 7% of by-product.

We claim:

1. A process for preparing monocarboxylic esters of the formula I

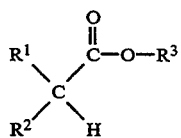

where
R¹ and R² are each hydrogen, C₁–C₁₂-alkyl, C₃–C₈-cycloalkyl, acyl, aryl or C₇–C₂₀-aralkyl or together —(CH₂)ₙ—X—(CH₂)ₘ—,
X is methylene, oxygen, sulfur, NH or NR³,
R³ is C₁–C₁₂-alkyl, and
n and m are each from 0 to 8,
which comprises reacting geminal dicarboxylic esters of the formula II

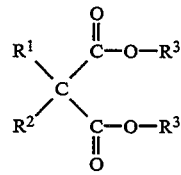

where R¹ to R³ are each as defined above, at from 150° to 400° C. in the presence of one or more catalysts selected from the group consisting of boron trioxide, aluminum oxide, silicon dioxide, titanium dioxide, zinc oxide, niobium oxide, vanadium pentoxide, molybdenum oxide, tungsten oxide, zirconium dioxide, oxides of chromium, oxides of the elements of the lanthanide series of the periodic table of the elements, zeolites, and heteropoly acids.

2. A process as claimed in claim 1, wherein the catalysts used are zeolites or heteropoly acids.

3. A process as claimed in claim 1, wherein the reaction is carried out in the gas phase.

4. A process as claimed in claim 1, wherein R¹ and R² are together —(CH₂)ₙ—X—(CH₂)ₘ—, X is methylene, oxygen, sulfur, NH or NR³, R³ is C₁–C₁₂-alkyl, and n and m are each from 0 to 8 in the formulae I and II.

5. A process as claimed in claim 1, wherein $R^1$ and $R^2$ are together —$(CH_2)_2$—O—$(CH_2)_2$— in the formulae I and II.

6. A process as claimed in claim 1, wherein the catalyst is one or more members selected from the group consisting of aluminum oxide, silicon dioxide, titanium dioxide, zirconium dioxide, vanadium pentoxide, boron trioxide, oxides of chromium, oxides of molybdenum, and oxides of tungsten.

* * * * *